US00PP34978P2

(12) United States Plant Patent
White

(10) Patent No.: US PP34,978 P2
(45) Date of Patent: Feb. 14, 2023

(54) PEAR TREE NAMED 'PREMP099'

(50) Latin Name: ***P.* x *bretschneideri* x (((*P.* x *bretschneideri*) x *Pyrus pyrifolia*)**
Varietal Denomination: PremP099

(71) Applicant: Prevar Limited, Hastings (NZ)

(72) Inventor: Allan G. White, Hastings (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 17/803,557

(22) Filed: Aug. 26, 2022

(51) Int. Cl.
*A01H 5/08* (2018.01)
*A01H 6/74* (2018.01)

(52) U.S. Cl.
USPC ..... Plt./178

(58) Field of Classification Search
USPC ..... Plt./156, 176, 178
See application file for complete search history.

*Primary Examiner* — Karen M Redden
(74) *Attorney, Agent, or Firm* — Michelle Bos Legal LLC

(57) ABSTRACT

A new Asian-type pear tree notable for its fruit, which exhibits attractive coloring, mildly sweet hazelnut flavor, and good storage and shelf life.

4 Drawing Sheets

Latin name: *P.* x *bretschneideri* x (((*P.* x *bretschneideri*) x *Pyrus pyrifolia*).

Variety denomination: PremP099.

BACKGROUND OF THE VARIETY

'PremP099' is a new and distinct Asian-type pear tree, originating from a controlled cross of 'Yali' (female parent, not patented) x 'Hwa Hong' (male parent, not patented). The cross was made at Motueka, New Zealand in 1994. 'PremP099' was first asexually propagated by grafting at Appleby, New Zealand in 1999. The variety has been observed to remain true to type over successive asexually propagated generations.

BRIEF DESCRIPTION OF THE VARIETY

'PremP099' was first selected for its attractive fruit with sweet hazelnut flavor and good storage and shelf life. Fruit of 'PremP099' has a more pronounced blush than the fruit of parent varieties 'Yali' and 'Hwa Hong.' Trees of 'PremP099' exhibit somewhat less vigor than the parent varieties. Further comparisons of 'PremP099' to parents 'Yali' and 'Hwa Hong' and to similar variety 'PremP003' (U.S. Plant Pat. No. 28,853) are provided in Table 1 and Table 2 below.

TABLE 1

Comparison of 'PremP099' to 'Yali' and 'Hwa Hong'

| | 'PremP099' | 'Yali' | 'Hwa Hong' |
|---|---|---|---|
| Vigor | Moderate | High | High |
| Fruit lenticels | Large, dense | Small, pronounced | Inconspicuous |
| Blush | Occasionally present | Absent | Absent |
| Russeting at stem end | Present | Minimal | Minimal |
| Harvest maturity | Early | Late | Mid-season |

TABLE 2

Comparison of 'PremP099' to 'PremP003'

| | 'PremP099' | 'PremP003' |
|---|---|---|
| Habit | Semi-spreading | Upright |
| Fruit lenticels | Large, dense | Small, pronounced |
| Blush | Occasionally present | Absent |
| Russeting around eye basin | Present | Minimal |
| Harvest maturity | Early | Mid-season |

BRIEF DESCRIPTION OF THE PHOTOGRAPHS

The attached photographs were taken during the 2021 and 2022 growing seasons near Wapato, Wash. The trees shown in the photographs were planted in 2016.

DETAILED BOTANICAL DESCRIPTION OF THE VARIETY

Figure 1:
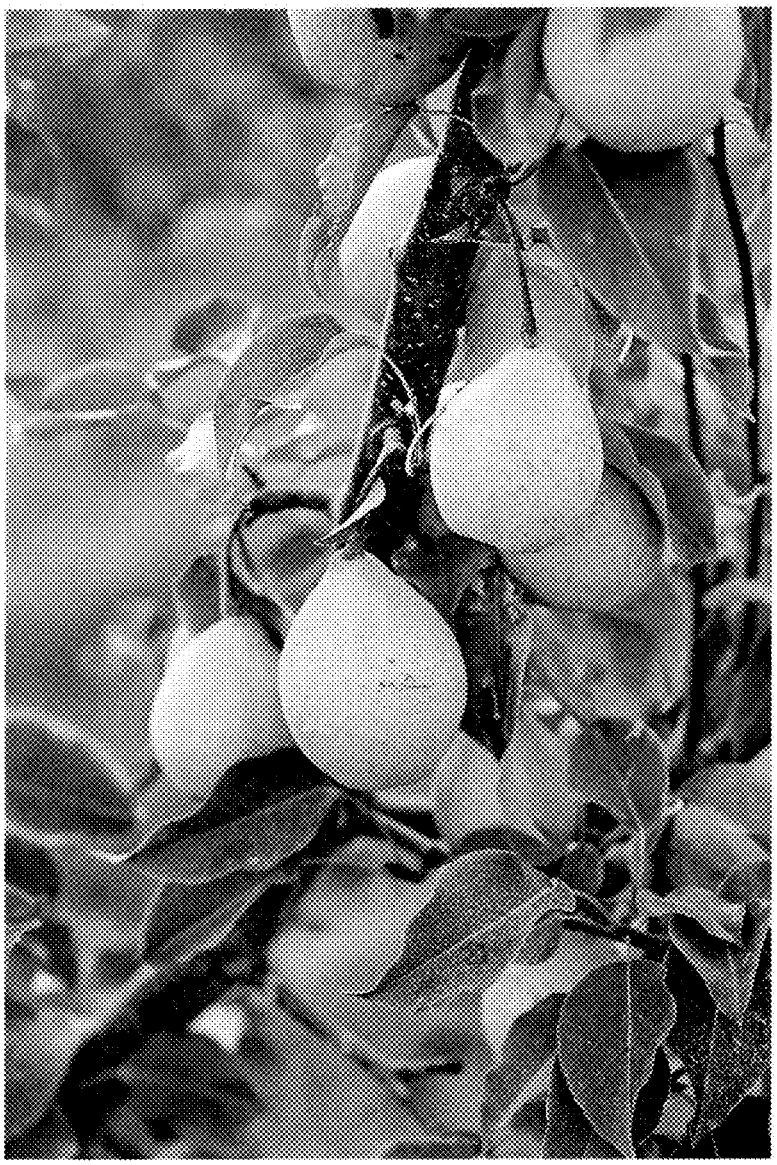
FIG. 1 shows fruits, leaves and branches on a 'PremP099' pear tree.
Figure 2:
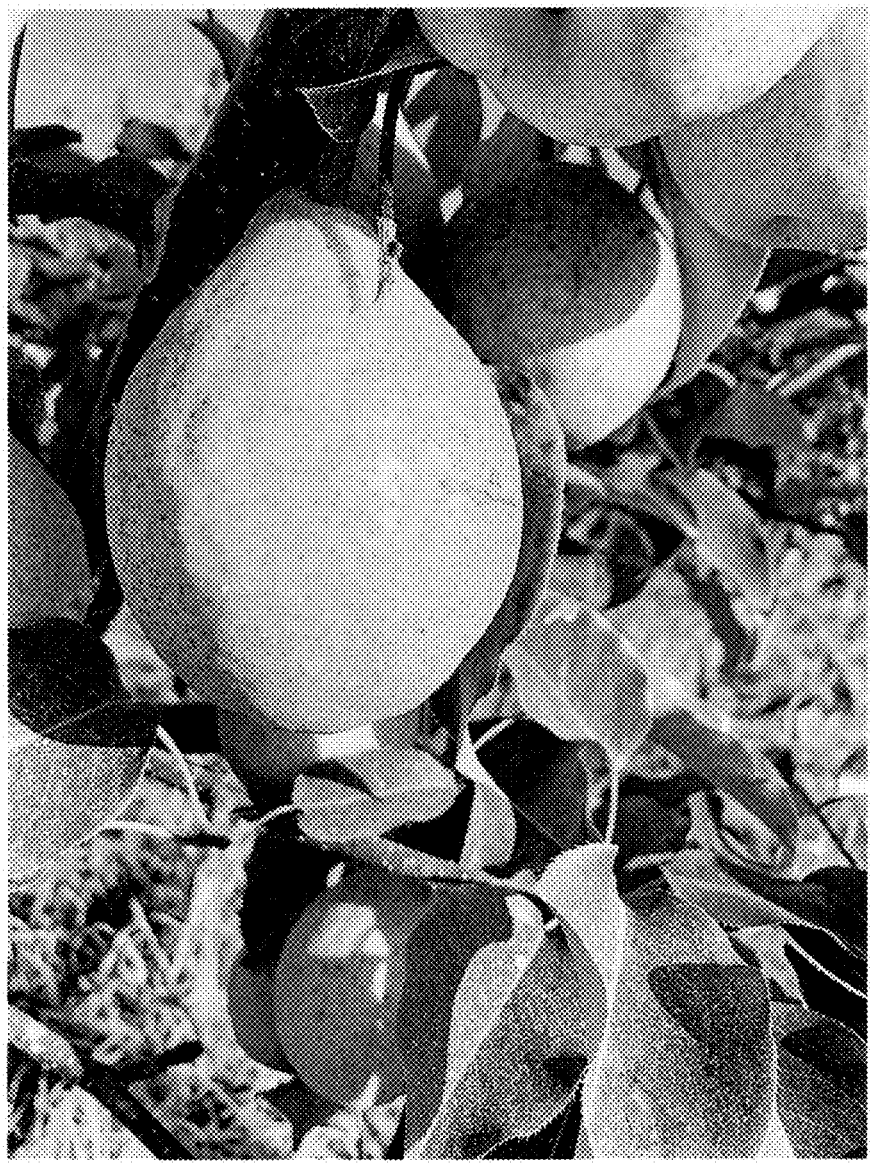
FIG. 2 shows fruits and leaves on a 'PremP099' pear tree.
Figure 3:
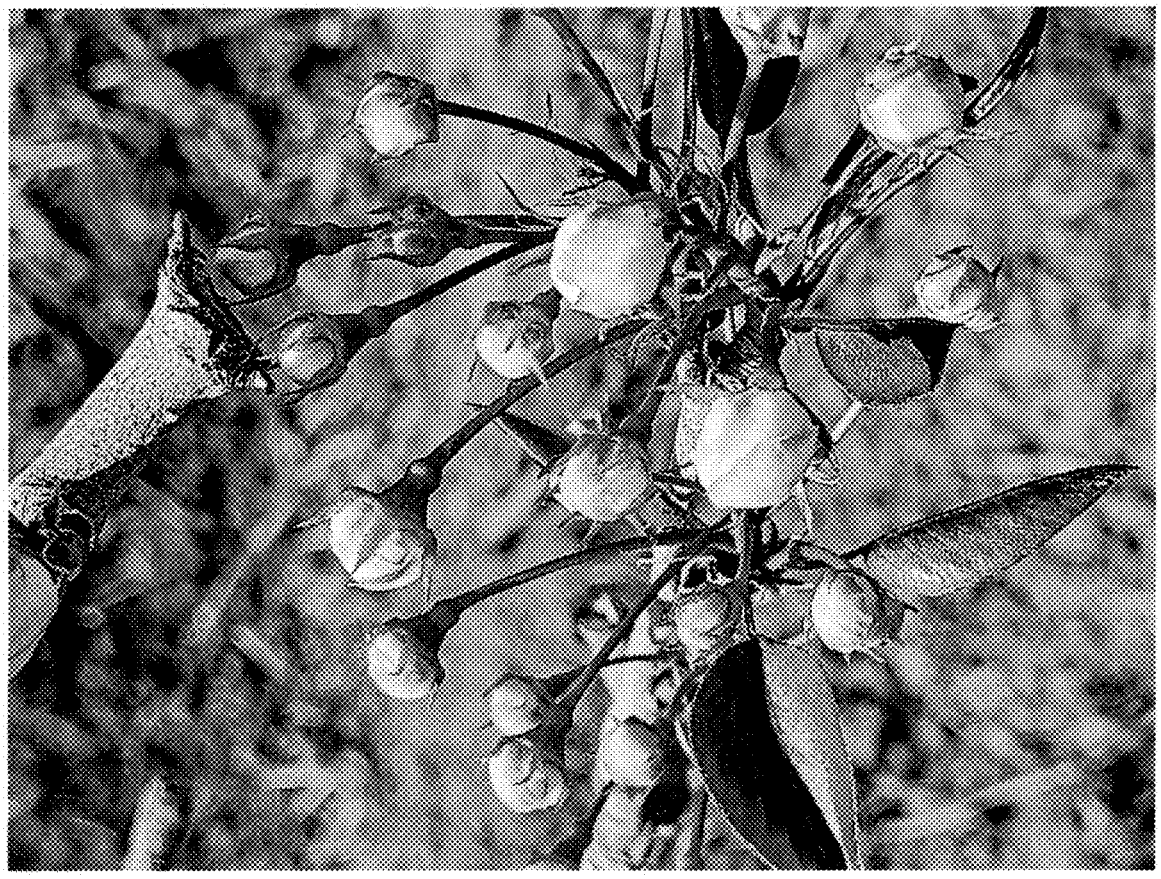
FIG. 3 shows flower buds and leaflets on a 'PremP099' pear tree.
Figure 4:
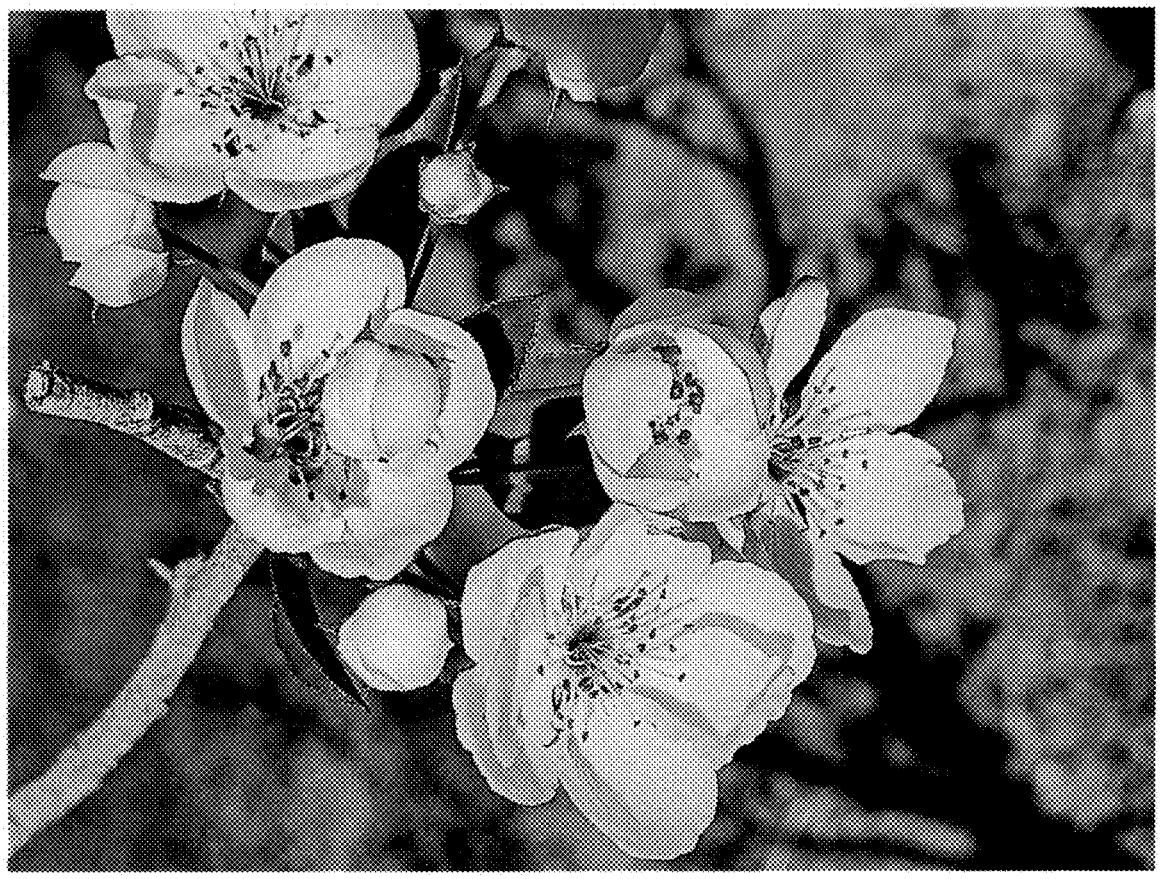
FIG. 4 shows flowers on a 'PremP099' pear tree.

The following detailed botanical description is based on observations made during the 2021 and 2022 growing seasons at Wapato, Wash. of 'PremP099' trees on 'Old Home x Farmingdale 97' rootstock (not patented), planted in 2016. Colors descriptions are made with reference to The R.H.S. Colour Chart, 4$^{th}$ ed. (Royal Horticultural Society, 2001). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor*.—Medium.
*Type*.—Ramified.
*Habit*.—Semi-spreading.
*Height*.—3 m.
*Spread*.—1.2 m.
*Trunk diameter at* 30 *cm above the graft*.—6 cm.
*Bark texture*.—Smooth with prominent lenticels.
*Bark color*.—Greyed-orange 166A.
*Lenticel length*.—2 mm.
*Lenticel width*.—2 mm.
*Lenticel shape*.—Round.
*Lenticel color*.—White N155A.
*Lenticel density per* 10 $cm^2$.—20 to 25.

Branch (fruiting branches located at around 1 m above the graft union):
*Length*.—33 cm.
*Diameter*.—1 cm.
*Crotch angle*.—90°.
*Bark color*.—Brown 200D.
*Lenticel length*.—2 mm.
*Lenticel width*.—1 mm.
*Lenticel shape*.—Oval.
*Lenticel color*.—White N155A.
*Lenticel density per* $cm^2$.—About 15.

One year old shoot:
*Length*.—80 cm.
*Diameter*.—1 cm.
*Color*.—Greyed-orange 166B.
*Pubescence*.—None.
*Internode length*.—5 cm.
*Lenticel length*.—2 mm.
*Lenticel width*.—1 mm.
*Lenticel shape*.—Oval.
*Lenticel color*.—White 155B.
*Lenticel density per* $cm^2$.—About 15.
*Vegetative bud shape*.—Elongated.
*Position of vegetative buds in relation to shoot*.—Upward.

Flower buds:
*Stage described*.—Bud burst.
*Quantity per spur*.—8.
*Bud shape*.—Round.
*Apex shape*.—Pointed.
*Length*.—14 mm.
*Diameter*.—17 mm.
*Color*.—Red-purple 63C and 155A white.

Flowers:
*Diameter of fully open flower*.—4 cm.
*Depth of open flower*.—20 mm.
*Relative position of petal margin*.—Overlapping.
*Number per cluster*.—9.
*Date of first bloom*.—Apr. 2 (2022).
*Date of full bloom*.—Apr. 7 (2022).
*Pollination requirement*.—Pollinator required.

Petals:
*Number per flower*.—5.
*Shape*.—Orbicular.
*Length*.—15 mm.
*Width*.—12 mm.
*Apex shape*.—Rounded.
*Base shape*.—Cuneate.
*Margin*.—Entire, undulating.
*Color of upper surface*.—White NN155C tinged with violet 84C at outer edge.
*Color of lower surface*.—White NN155C.

Pistils:
*Length*.—9 mm.
*Color*.—Yellow-green 145C.

Stigma:
*Diameter*.—1 mm.
*Color*.—Yellow-green 145C.

Style:
*Length*.—8 mm.
*Color*.—Yellow-green 145C.

Ovary:
*Length*.—4 mm; width 2 mm.
*Color*.—Yellow-green 145B.

Stamens:
*Quantity*.—19.
*Length*.—9 mm.
*Anther color*.—Grey-brown N199B and red-purple 61A.
*Presence of pollen*.—Present, scarce.
*Pollen color*.—Red-purple 61A.

Pedicel:
*Length*.—35 mm.
*Diameter*.—2 mm.
*Color*.—Yellow-green 145B.

Sepals:
*Quantity*.—5.
*Color*.—Yellow-green 145C near base; 63B near tip.
*Length*.—7 mm.
*Width*.—1 mm at tip to 4 mm at base.
*Shape*.—Triangular.
*Apex shape*.—Pointed.
*Margin*.—Entire.

Leaves:
*Shape*.—Ovate.
*Length*.—10 cm.
*Width*.—5 cm.
*Length/width ratio*.—2:1.
*Blade margin*.—Serrate.
*Apex shape*.—Acuminate.
*Base shape*.—Rounded.
*Color of upper surface*.—Green NN137D.
*Color of lower surface*.—Green 139D.
*Vein color*.—Yellow-green 149B.
*Venation pattern*.—Reticulate, typical of Asian pear trees.
*Attitude in relation to shoot*.—Upward.
*Curvature of longitudinal axis*.—Central vein convex, with sides of leaf folded slightly upward.

Petiole:
*Length*.—3 cm.
*Diameter*.—2 mm.
*Color*.—Upper yellow-green 149B.
*Stipule*.—Absent.

Fruit:
*Quantity per cluster*.—3 to 5 after thinning.
*Height*.—9 cm.
*Diameter*.—7 cm.
*Weight*.—Average 198 g.
*General shape in profile*.—Globose-conical; typical of Asian pears.
*Position of maximum diameter*.—Equator.
*Symmetry in longitudinal section*.—Symmetrical.
*Profile of sides*.—Convex.

*Skin texture*.—Smooth.
*Background color of skin*.—Yellow-green N144B.
*Over color of skin*.—Yellow 4C.
*Amount of over color of skin*.—95%.
*Pattern of overcolor*.—Solid flush.
*Intensity of over color of skin*.—Intense.
*Lenticels*.—Dense, circular shape, prominent.
*Relative area of russet around eye basin*.—None.
*Relative area of russet on cheeks*.—Minimal.
*Relative area of russet on stalk attachment*.—Present.
*Length of stalk*.—5 cm.
*Diameter of stalk*.—5 mm.
*Curvature of stalk*.—Slightly curved.
*Attitude of stalk in relation to axis of fruit*.—Straight to somewhat angled.
*Stalk color*.—Greyed-orange 166B.
*Depth of eye basin*.—5 mm.
*Width of eye basin*.—15 mm.
*Attitude of sepals at harvest*.—Erect.
*Firmness of flesh*.—Firm.
*Flesh texture*.—Crisp, slightly fibrous.
*Aroma*.—Mild.
*Flavor*.—Sweet, notes of hazelnut.
*Juiciness*.—Moderate.
*Brix*.—11.
*Flesh color*.—White N155A.

Seeds:
*Quantity per fruit*.—10.
*Shape*.—Oval with pointed ends.
*Length*.—12 mm.
*Width*.—5 mm.
*Color*.—Greyed-orange 177A.

Harvest:
*Harvest date*.—Aug. 25 (2021).
*Number of picks*.—1.

Disease resistance/susceptibility:
*Winter hardiness*.—Hardy in area tested.
*Market use*.—Fresh.
*Storage characteristics*.—Good storage and shelf life.

The invention claimed is:

1. A new and distinct pear tree named 'PremP099' substantially as illustrated and described herein.

* * * * *